US012655381B2

(12) United States Patent
Frigård et al.

(10) Patent No.: US 12,655,381 B2
(45) Date of Patent: Jun. 16, 2026

(54) FLUID COUPLING NETWORK FOR SAMPLING A BIOREACTOR

(71) Applicant: CYTIVA SWEDEN AB, Uppsala (SE)

(72) Inventors: Tuomo Frigård, Uppsala (SE); Camilla Estmer Nilsson, Uppsala (SE); Patricia Roch, Uppsala (SE); Björn Markus Olovsson, Uppsala (SE); Magnus Wetterhall, Uppsala (SE); Nils Stafström, Uppsala (SE); Inger Salomonsson, Uppsala (SE)

(73) Assignee: CYTIVA SWEDEN AB, Uppsala (SE)

( * ) Notice: Subject to any disclaimer, the term of this patent is extended or adjusted under 35 U.S.C. 154(b) by 627 days.

(21) Appl. No.: 18/044,859

(22) PCT Filed: Oct. 13, 2021

(86) PCT No.: PCT/EP2021/078273
§ 371 (c)(1),
(2) Date: Mar. 10, 2023

(87) PCT Pub. No.: WO2022/089938
PCT Pub. Date: May 5, 2022

(65) Prior Publication Data
US 2023/0357702 A1     Nov. 9, 2023

(30) Foreign Application Priority Data

Oct. 29, 2020    (GB) ...................................... 2017182

(51) Int. Cl.
| | |
|---|---|
| *C12M 1/36* | (2006.01) |
| *C12M 1/00* | (2006.01) |
| *C12M 1/12* | (2006.01) |

(52) U.S. Cl.
CPC ............ *C12M 41/48* (2013.01); *C12M 23/40* (2013.01); *C12M 37/00* (2013.01)

(58) Field of Classification Search
CPC ...... C12M 41/48; C12M 23/40; C12M 37/00; G01N 1/10; G01N 2001/1037
See application file for complete search history.

(56) References Cited

U.S. PATENT DOCUMENTS

| | | |
|---|---|---|
| 4,918,019 A | 4/1990 | Guinn |
| 2010/0144037 A1 | 6/2010 | Antwiler |

(Continued)

FOREIGN PATENT DOCUMENTS

| | | |
|---|---|---|
| JP | 2012-88127 A | 5/2012 |
| JP | 2020-65470 A | 4/2020 |
| WO | 2020/152509 A1 | 7/2020 |

OTHER PUBLICATIONS

PCT International Search Report and Written Opinion for PCT/EP2021/078273, mailed Mar. 21, 2022 (20 pages).

(Continued)

*Primary Examiner* — Michael L Hobbs
(74) *Attorney, Agent, or Firm* — Eversheds-Sutherland (US) LLP

(57) ABSTRACT

The present invention relates to a computer implemented method for controlling a fluid coupling network (170), the fluid coupling network (170) being configured to be fluidly couplable to bioreactor (110), a gas source (120), a buffer source (140), a waste port (150), a processing system (160) and a conduit reservoir (208), the fluid coupling network (170) comprising a barrier unit (220) configured to sterilely separate fluid paths within the fluid coupling network (170), the fluid coupling network (170) being controllable to sample the bioreactor (110), the method comprising obtaining (510) a fluid sample from the bioreactor (110), wherein the step of obtaining the fluid sample comprises controlling a flow of fluid from the bioreactor (110) via the conduit reservoir (208) and the fluid coupling network (170) to the waste port (150), to fill the conduit reservoir (208) with the fluid from the bioreactor (110), providing (530) the fluid sample, wherein the step of providing the fluid sample comprises to provide the fluid sample to the processing system (160) from the conduit reservoir (208) via the fluid coupling network (170), and returning (540) residual fluid (Continued)

sample to the bioreactor (110), wherein the residual fluid sample is comprised by a part of the fluid coupling network (170) separated by the barrier unit (220), wherein the step of returning residual fluid sample comprises controlling a flow of gas from a gas source (120) to the bioreactor (110) via the part of the fluid coupling network (170).

22 Claims, 9 Drawing Sheets

(56)                    References Cited

U.S. PATENT DOCUMENTS

| | | |
|---|---|---|
| 2014/0087413 A1 | 3/2014 | Newbold et al. |
| 2014/0123777 A1 | 5/2014 | Newbold et al. |
| 2016/0122798 A1* | 5/2016 | Zhang ..................... G01N 1/18 |
| | | 435/309.1 |
| 2016/0122978 A1 | 5/2016 | Matusu et al. |
| 2016/0123848 A1 | 5/2016 | Griffin et al. |
| 2019/0292507 A1 | 9/2019 | Stone et al. |
| 2020/0123489 A1* | 4/2020 | Makino ................. C12M 41/00 |

OTHER PUBLICATIONS

GB Search Report for GB 2017182.3, mailed Apr. 22, 2021 (6 pages).
First Office Action in corresponding Japanese Patent Application No. 2023-526445, dated Sep. 16, 2025, 8 pages.

* cited by examiner

100

500

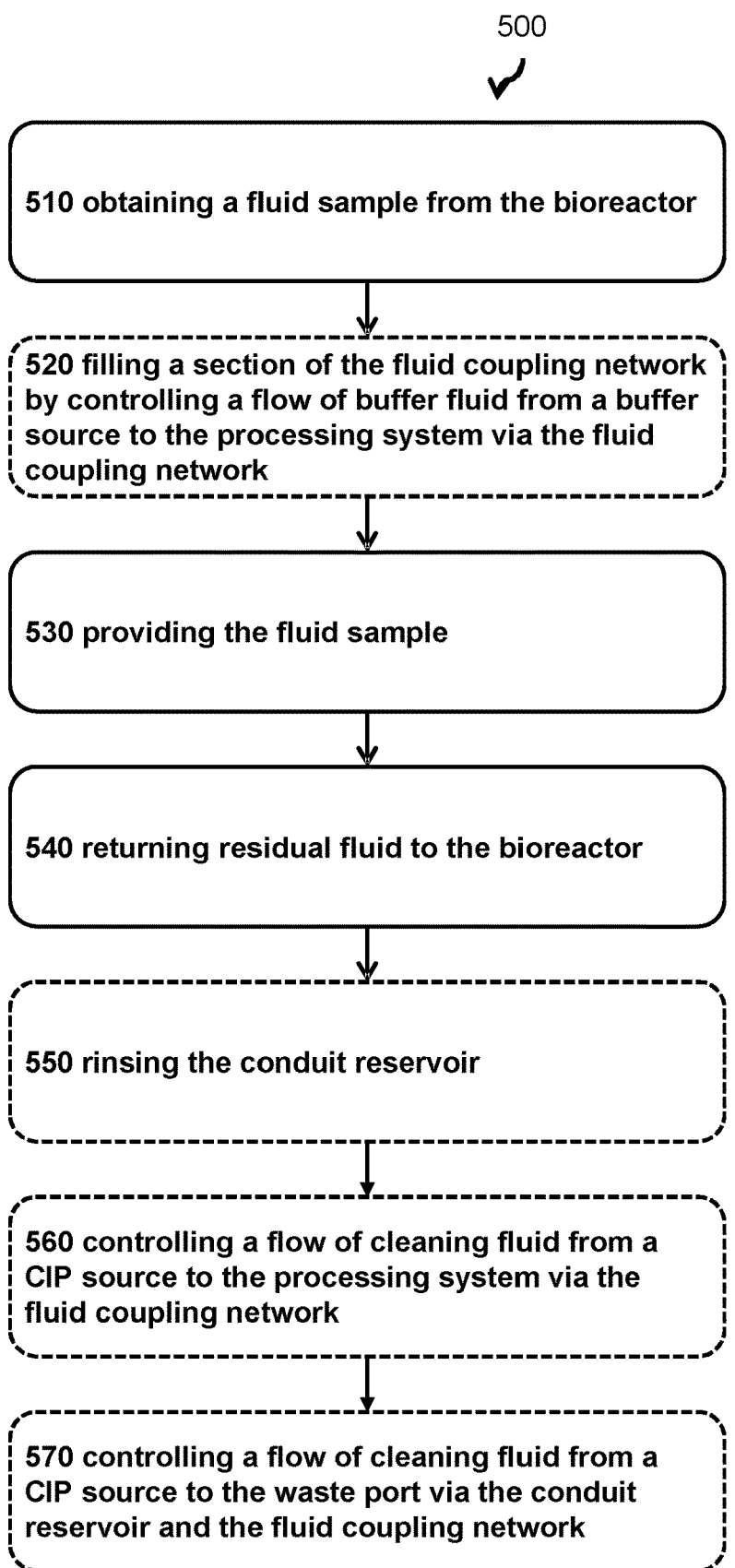

510 obtaining a fluid sample from the bioreactor 520 filling a section of the fluid coupling network by controlling a flow of buffer fluid from a buffer source to the processing system via the fluid coupling network 530 providing the fluid sample 540 returning residual fluid to the bioreactor 550 rinsing the conduit reservoir 560 controlling a flow of cleaning fluid from a CIP source to the processing system via the fluid coupling network 570 controlling a flow of cleaning fluid from a CIP source to the waste port via the conduit reservoir and the fluid coupling network

Fig. 5

FLUID COUPLING NETWORK FOR SAMPLING A BIOREACTOR

CROSS REFERENCE TO RELATED APPLICATIONS

This application claims the priority benefit of PCT/EP2021/078273, filed Oct. 13, 2021, which claims the priority benefit to GB Application No. 2017182.3, filed Oct. 29, 2020, the entire contents of which are incorporated herein by reference.

TECHNICAL FIELD

The present invention relates to a fluid coupling network being controllable to sample a bioreactor. The invention further relates to a method, a barrier unit, a control unit, a computer program and a computer program product.

BACKGROUND

A bioreactor is typically a vessel in which a chemical process is carried out which involves organisms or biochemically active substances derived from such organisms. In the biotechnology industry, frequent use is made of bioreactors, sometimes operating over longer time. In particular, bioreactors are used in the biotechnology industry for growing organisms such as cells, bacteria, or fungi. The organisms may produce substances such as biomacromolecules (e.g. proteins) or various types of viruses/parts of viruses. In such bioreactors suitable for producing organisms or biochemically active substances, there is a need for periodic sampling of the fluid in the bioreactor. It is then important to avoid contamination and/or loss of sterility during such a sampling event. In other words, it is necessary to avoid contamination of the vessel or the contained environment itself during sampling. The sampling is required e.g. to monitor and control the conditions and levels of nutrients needed for cell growth.

Conventionally, sampling of the bioreactor may be performed manually, typically performed by the use of a hypodermic needle injected through a membrane. Manual sampling can be a time consuming and expensive process and increases the risk of the bioreactor fluid to become contaminated.

Some conventional systems include automated sampling of the bioreactor, such as the sampling system described in document US2014087413A1. However, this conventional approach has the disadvantage of wasting a relatively large volume of fluid each time a fluid sample is obtained.

There is therefore a need for an improved method and fluid network for sampling of a bioreactor.

OBJECTS OF THE INVENTION

An objective of embodiments of the present invention is to provide a solution which mitigates or solves the drawbacks and problems described above.

SUMMARY OF THE INVENTION

The above objective is achieved by the subject matter described herein. Further advantageous implementation forms of the invention are further defined herein.

According to a first aspect of the invention, the above mentioned and other objectives are achieved by a computer implemented method for controlling a fluid coupling network, the fluid coupling network being configured to be fluidly couplable to bioreactor, a gas source, a buffer source, a waste port, a processing system and a conduit reservoir, the fluid coupling network comprising a barrier unit configured to sterilely separate fluid paths within the fluid coupling network, the fluid coupling network being controllable to sample the bioreactor, the method comprising obtaining a fluid sample from the bioreactor, wherein the step of obtaining the fluid sample comprises controlling a flow of fluid from the bioreactor via the conduit reservoir and the fluid coupling network to the waste port, to fill the conduit reservoir with the fluid from the bioreactor, providing the fluid sample, wherein the step of providing the fluid sample comprises to provide the fluid sample to the processing system from the conduit reservoir via the fluid coupling network, and returning residual fluid sample to the bioreactor, wherein the residual fluid sample is comprised by a part of the fluid coupling network separated by the barrier unit, wherein the step of returning residual fluid sample comprises controlling a flow of gas from a gas source to the bioreactor via the part of the fluid coupling network.

An advantage of the embodiment according to the first aspect is that the risk of contamination is reduced or minimized. A further advantage is that the required volume of fluid drawn from the bioreactor is reduced.

According to a second aspect of the invention, the above mentioned and other objectives are achieved by a fluid coupling network, the fluid coupling network being configured to be fluidly couplable to bioreactor, a gas source, a buffer source, a waste port a processing system and a conduit reservoir, the fluid coupling network comprising a barrier unit configured to sterilely separate fluid paths within the fluid coupling network, the fluid coupling network being controllable to sample the bioreactor, wherein the fluid coupling network is configured to obtain a fluid sample, wherein the fluid sample is obtained by enabling a flow of fluid from the bioreactor by providing a fluid path from the bioreactor via the conduit reservoir (208) to the waste port, to fill the conduit reservoir with fluid from the bioreactor, provide the fluid sample, wherein the fluid sample is provided to the processing system (160) by providing a fluid path from the conduit reservoir to the processing system, and return residual fluid sample to the bioreactor, wherein the residual fluid sample is comprised by a part of the fluid coupling network separated by the barrier unit, wherein the residual fluid sample is returned by providing a fluid path from the gas source to the bioreactor, wherein the barrier unit is configured to sterilely separate the part of the fluid coupling network, the part comprising fluid paths that fluidly couple the bioreactor and the gas source.

According to a third aspect of the invention, the above mentioned and other objectives are achieved by a barrier unit configured to sterilely separate fluid paths within a fluid coupling network, wherein the barrier unit sterilely separates fluid paths of part of the fluid coupling network from fluid paths of a remaining part of the fluid coupling network, wherein the barrier unit, operating in a first operational state, allows fluid to flow from the part of the fluid coupling network to the remaining part of the fluid coupling network and the barrier unit, operating in a second operational state, prevents fluid to flow from the part of the fluid coupling network to the remaining part of the fluid coupling network.

According to a fourth aspect of the invention, the above mentioned and other objectives are achieved by a control unit for a fluid coupling network being controllable to sample a bioreactor, the control unit comprising processing circuitry, a memory comprising instructions executable by the processing circuitry, causing the processing circuitry to perform the method according to the first aspect.

According to a fifth aspect of the invention, the above mentioned and other objectives are achieved by a computer program comprising computer-executable instructions for causing a control unit, when the computer-executable instructions are executed on processing circuitry comprised in the control unit, to perform any of the method steps according to the first aspect. According to a sixth aspect of the invention, the above mentioned and other objectives are achieved by a computer program product comprising a computer-readable storage medium, the computer-readable storage medium having the computer program according to the fifth aspect embodied therein.

Advantages of embodiments according to the second to sixth aspect are at least the same as for the first aspect.

Further applications and advantages of embodiments of the invention will be apparent from the following detailed description.

BRIEF DESCRIPTION OF THE DRAWINGS

FIG. 5 shows a flowchart of a method according to one or more embodiments of the present disclosure.

Figure 1:
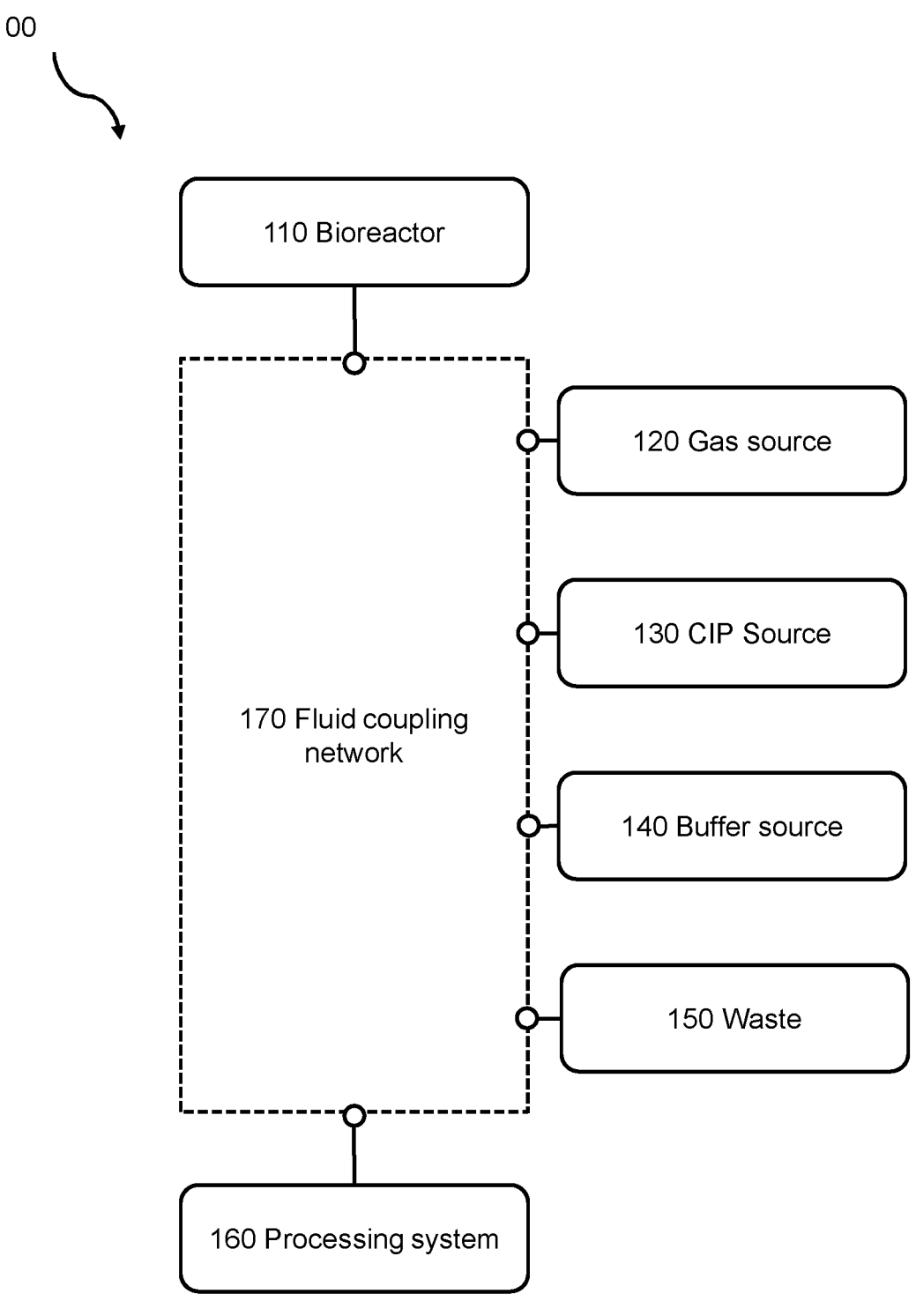
FIG. 1 shows a bioprocessing system comprising a fluid coupling network according to one or more embodiments of the present disclosure.

A more complete understanding of embodiments of the invention will be afforded to those skilled in the art, as well as a realization of additional advantages thereof, by a consideration of the following detailed description of one or more embodiments. It should be appreciated that like reference numerals are used to identify like elements illustrated in one or more of the figures.

DETAILED DESCRIPTION

An "or" in this description and the corresponding claims is to be understood as a mathematical OR which covers "and" and "or", and is not to be understand as an XOR (exclusive OR). The indefinite article "a" in this disclosure and claims is not limited to "one" and can also be understood as "one or more", i.e., plural.

In the present disclosure, the term "bioreactor" denotes a vessel/container configured for having a chemical process carried out within the vessel, which process involves organisms or biochemically active substances derived from such organisms. Examples of bioreactors are single use reactors (e.g. Cytiva WAVE/Xcellerex), stainless steel reactors.

Examples of process modes used in the bioreactors include perfusion culturing, fed batch culturing and batch culturing.

In the present disclosure, the term "fluid coupling network" denotes an arrangement for providing fluid paths to/from a bioreactor, typically from a bioreactor to a bioprocessing system or a bioanalytical system, such as a chromatograph.

In the present disclosure the term "fluid path" denotes an assembly of components configured to/for conveying a fluid, e.g. conduits fluidly coupled to one or more fluid valves. The fluid path typically comprises one or more conduits connecting fluid inlets and fluid outlets and any intermediate equipment, such as filters, ventilators, sensors, valves etc.

In the present disclosure, the term "gas source" denotes an arrangement for providing gas, e.g. a canister of compressed air.

In the present disclosure, the term "buffer source" denotes an arrangement for providing buffer fluid, e.g. containers and/or pumps arranged to provide the buffer fluid. Buffer fluid may e.g. include Phosphate, Acetate, TRIS, Citrate, HEPES, Acetonitrile, Methanol, Formic acid, Tri-Fluoro-acetic acid TFA, salts and/or Additives (detergents).

In the present disclosure, the term "clean in place source" or "CIP source" denotes an arrangement for providing CIP fluid, e.g. containers and/or pumps arranged to provide the CIP fluid. Examples of CIP fluids are Oxidizing agents (NaClO, peracetic acid, $H_2O_2$), Organic solvents (IPA, EtOH), Acids ($HNO_3$, HAc), Bases (NaOH) and Steam.

In the present disclosure the term "waste port" or simply "waste" denotes an arrangement for receiving fluid, such as a drain, a container or other receptacle. The waste port may e.g. comprise a valve or a check valve that is controlled/switched to an open/closed operational state.

In the present disclosure, the term "processing system" denotes equipment for processing the sample from the bioreactor, e.g. a group of instruments, a chromatography system or a filtration unit.

In the present disclosure the term "conduit reservoir" denotes an arrangement for holding the sample from the bioreactor, e.g. a looped conduit, a container, a tube, a syringe, an air trap or a superloop. An important feature of the "conduit reservoir" is that it is arranged to allow cleaning by letting a fluid flow through the entire reservoir. By using a reservoir with substantially the same cross-section area, the entire reservoir is effectively cleaned. This is e.g. the case for the variable sample volume reservoir Superloop™ from Cytiva. In other words, preferably the "conduit reservoir" is a "looped conduit reservoir", allowing cleaning fluid to flow through and clean the reservoir.

In the present disclosure, the term "controllable valve" denotes an arrangement or apparatus being configured to allow or prevent fluid, received from at an inlet of the controllable valve to an outlet of the controllable valve. The controllable valve typically comprises a valve unit, an actuator unit and control logics, which control logics are capable of receiving a control signal and control the actuator unit to move the valve to an open operational state where fluid is fully allowed to flow from the inlet to the outlet, to a closed operational state where fluid is prevented to flow from the inlet to the outlet or optionally to an intermediate operational state where a reduced flow is allowed from the inlet to the outlet. In all the embodiments described herein changes of operational states of the controllable valves are made in response to a received control signal. In one example a control unit sends a control signal indicative of a desired operational state to a controllable valve.

As mentioned in the background section, conventional sampling of a bioreactor is time consuming and may contaminate the process in the bioreactor. The sampling typically allows measurement of characteristics of the fluid in the bioreactor, such as cell count, oxygen levels, PH levels etc.

The present disclosure improves the sampling process by providing a controllable fluid coupling network and a method controlling the fluid coupling network. A sample is obtained, held in the conduit reservoir, and then provided to a processing system, typically for determining characteristics of the bioreactor fluid. The disclosure then reduces the impact of sampling by returning residual fluid to the bioreactor, thereby reducing the volume of fluid removed from the bioreactor. The present disclosure then prepares the controllable fluid coupling network for the next sampling occurrence by cleaning the controllable fluid coupling network.

FIG. 1 shows a bioprocessing system 100 comprising a fluid coupling network 170 according to one or more embodiments of the present disclosure. The fluid coupling network 170 is configured to be fluidly couplable to a bioreactor 110, a gas source 120, a buffer source 140, a waste port 150, a processing system or a fluid sample processing system 160 and a conduit reservoir 208. The fluid coupling network 170 further comprises a barrier unit 220 configured to sterilely separate fluid paths within the fluid coupling network 170. The fluid coupling network 170 is controllable to sample or to provide a fluid sample from the bioreactor 110.

The bioprocessing system 100 is formed by fluidly coupling the fluid coupling network 170 to the bioreactor 110, the gas source 120, the buffer source 140, the waste port 150, the processing system 160 and the conduit reservoir 208. The bioprocessing system 100 is further formed by communicatively coupling the fluid coupling network 170 to a control unit CU.

In a typical sampling cycle of the bioreactor 110, the system 100 is configured to control the fluid coupling network 170, by the control unit CU, to:

Obtain a fluid sample from the bioreactor 110, wherein the step of obtaining the fluid sample comprises controlling a flow of fluid from the bioreactor 110 via the conduit reservoir 208 and the fluid coupling network 170 to the waste port 150, to fill the conduit reservoir 208 with the fluid from the bioreactor 110. In other words, the fluid coupling network 170 is configured/controlled to provide a fluid path from the bioreactor 110 to a port couplable to the waste port 150 via the conduit reservoir 208. The conduit reservoir 208 may be a looped conduit, which can be selected/configured to have an inner diameter and/or length to contain a particular fluid sample volume required to measure/determine characteristics of the fluid sample. An advantage of this is that the volume may be adapted by cutting a conduit, such as a tubing, to a length matching the required sample volume.

The fluid coupling network 170 is then configured/controlled to provide the fluid sample. The fluid coupling network 170 provides the fluid sample to the processing system 160 from the conduit reservoir 208 via the fluid coupling network 170. In other words, the fluid coupling network 170 is configured/controlled to provide a fluid path from the conduit reservoir 208 to a port couplable to the processing system 160.

The fluid coupling network 170 is then configured/controlled to return residual fluid sample to the bioreactor 110. The residual fluid sample is comprised by a part/first part 1701 of the fluid coupling network 170 separated by the barrier unit 220. The step of returning residual fluid sample comprises controlling a flow of gas from a gas source 120 to the bioreactor 110 via the part/first part 1701 of the fluid coupling network 170. In other words, the fluid coupling network 170 is configured/controlled to provide a fluid path from the gas source 120 to a port couplable to the bioreactor 110.

To ensure that fluid paths, when providing/transporting the fluid sample from the conduit reservoir 208, are not comprising/containing unwanted fluids, such as air, such section/s of fluid paths are filled with buffer fluid.

In one embodiment, the fluid coupling network 170 is further configured/controlled to fill a section of the fluid coupling network by controlling a flow of buffer fluid from the buffer source 140 to the processing system 160 via the fluid coupling network 170. In other words, the fluid coupling network 170 is configured/controlled to provide a fluid path from the buffer source 140 to a port couplable to the processing system 160. This step prepares the fluid coupling network 170 for providing the fluid sample by ensuring that the fluid paths of the section of the fluid coupling network is filled with buffer fluid not unwanted fluids, such as air.

To ensure that the entire sample has been provided from the conduit reservoir 208, the conduit reservoir 208 may in a further embodiment be rinsed by using buffer fluid.

In one embodiment, the fluid coupling network 170 is further configured/controlled to rinse the conduit reservoir 208 by controlling a flow of buffer fluid from the buffer source 140 to the processing system 160 via the conduit reservoir 208 and the fluid coupling network 170. In other words, the fluid coupling network 170 is configured/controlled to provide a fluid path from the buffer source 140 to the processing system 160 via the conduit reservoir 208.

To prepare the fluid coupling network 170 for the next fluid sampling cycle, a cleaning fluid or clean in place, CIP, fluid is allowed to flow through the fluid coupling network 170.

In one embodiment, the fluid coupling network 170 is further configured/controlled to be fluidly couplable to a clean in place, CIP, source 130. The fluid coupling network 170 is further configured/controlled to clean the section of the fluid coupling network by controlling a flow of cleaning fluid from the CIP source 130 to the processing system 160 via the fluid coupling network 170. In other words, the fluid coupling network 170 is configured/controlled to provide a fluid path from the CIP source 130 to the processing system 160.

Additionally or alternatively, in one embodiment, the fluid coupling network 170 is further configured/controlled to cleaning the conduit reservoir 208 by controlling a flow of cleaning fluid from the CIP source 130 to the waste port 150 via the conduit reservoir 208.

In an exemplary embodiment the disclosure of FIG. 1 is implemented using controllable valves fluidly coupled by using conduits or tubing.

Figure 2:
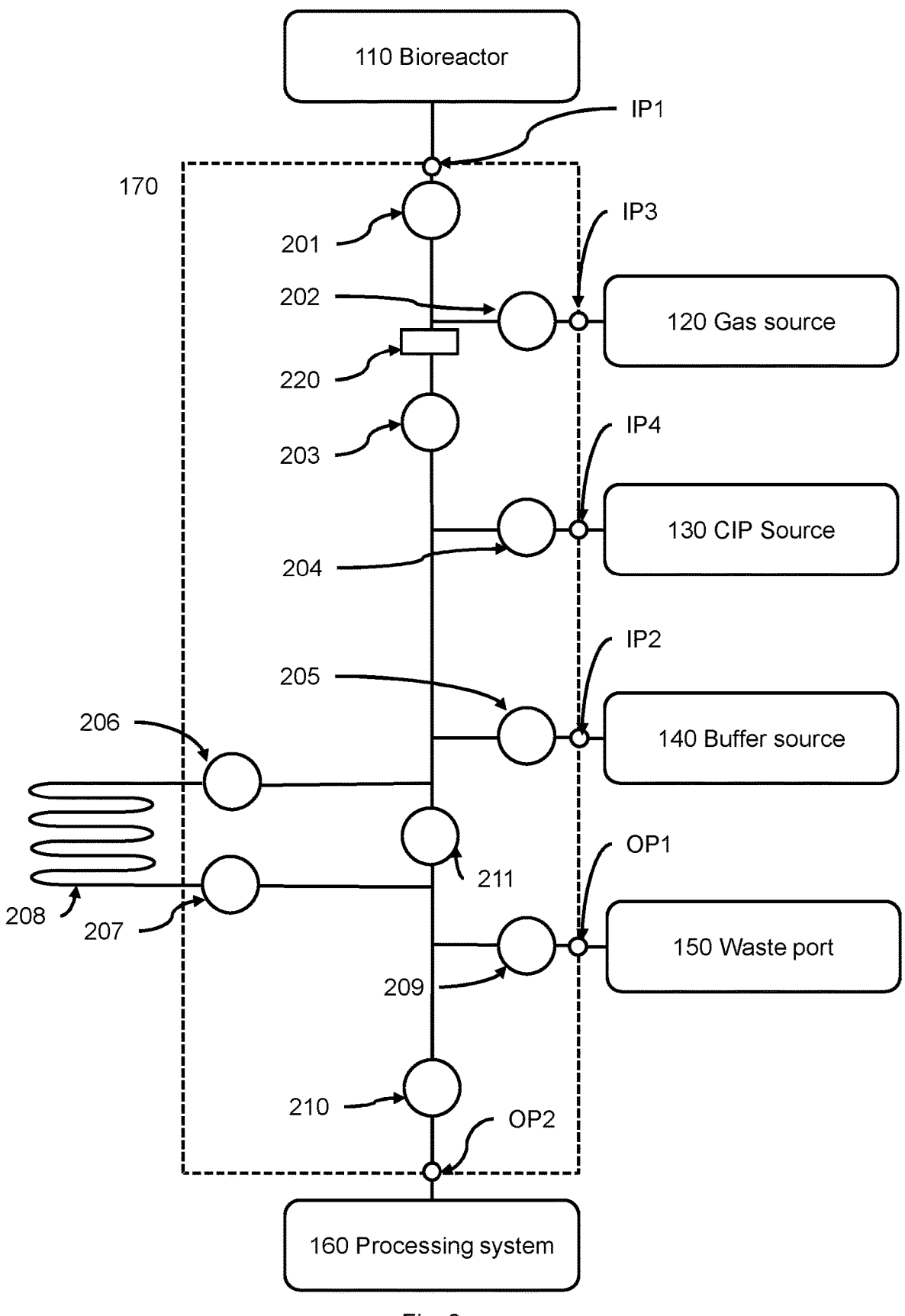
FIG. 2 shows details of the fluid coupling network according to one or more embodiments of the present disclosure.

FIG. 2 shows details of the fluid coupling network 170 according to one or more embodiments of the present disclosure. FIG. 2 illustrates how the barrier unit 220 is configured to separate the fluid coupling network 170 into a part/first part 1701 and a remaining part/second part 1702. The (first) part comprising fluid paths that fluidly couple the bioreactor 110 and the gas source 120 and the remaining (second) part comprising remaining fluid paths of the fluid coupling network 170.

The fluid coupling network 170 is configured to be fluidly couplable to bioreactor 110, a gas source 120, a buffer source 140, a waste port 150 a processing system 160 and a conduit reservoir 208. The fluid coupling network 170 further comprises a barrier unit 220 configured to sterilely separate fluid paths within the fluid coupling network 170. The barrier unit 220 is further described in relation to FIG. 6-9. The fluid coupling network 170 is controllable to sample the bioreactor 110. The fluid coupling network 170 is configured to:

Obtain a fluid sample, wherein the fluid sample is obtained by enabling a flow of fluid from the bioreactor 110 by providing a fluid path from the bioreactor 110 via the conduit reservoir 208 to the waste port 150, to fill the conduit reservoir 208 with fluid from the bioreactor 110.

Provide the fluid sample, wherein the fluid sample is provided to the processing system 160 by providing a fluid path from the conduit reservoir 208 to the processing system 160.

Return residual fluid sample to the bioreactor 110, where the residual fluid sample is comprised by a part/first part 1701 of the fluid coupling network 170 separated by the barrier unit 220. The residual fluid sample is returned by providing a fluid path from the gas source 120 to the bioreactor 110.

The barrier unit 220 is configured to sterilely separate the part of the fluid coupling network 170, the part comprising fluid paths that fluidly couple the bioreactor 110 and the gas source 120.

In one or more embodiments, the fluid coupling network 170 further comprises a first controllable valve 201 fluidly coupled to a first port IP1 couplable to the bioreactor 110 and being configured to allow or prevent fluid to flow between the bioreactor 110 and the fluid coupling network 170.

The fluid coupling network 170 further comprises a second controllable valve 206 fluidly coupled to an outlet of the first controllable valve 201, and an inlet of the conduit reservoir 208, and being configured to allow or prevent fluid, received from any of the first controllable valve 201 to flow to the conduit reservoir 208. Optionally, the fluid coupling network 170 further comprises a controllable valve 203 fluidly coupled between the first controllable valve 201 and the second controllable valve 206.

The fluid coupling network 170 further comprises a third controllable valve 207 fluidly coupled to an outlet of the conduit reservoir 208, and being configured to allow or prevent fluid to flow from the conduit reservoir 208.

The fluid coupling network 170 further comprises a fourth controllable valve 209 fluidly coupled to an outlet of the third controllable valve 207 and to a port OP1 couplable to the waste port 150 and being configured to allow or prevent fluid to flow from the outlet of the third controllable valve 207 to the waste port 150, wherein the fluid coupling network 170 is controlled to obtain a fluid sample and provide a fluid path by controlling the first controllable valve 201, the second controllable valve 206, the third controllable valve 207 and the fourth controllable valve 209 to an open operational state where fluid is allowed to flow. In other words, the fluid coupling network 170 is controlled to provide a fluid path from the first port IP1 couplable to the bioreactor 110 to the port OP1 couplable to the waste port 150.

Additionally or alternatively, the fluid coupling network 170 further comprises a fifth controllable valve 205 fluidly coupled to a second port IP2 couplable to the buffer source 140 and being configured to allow or prevent fluid to flow from the buffer source 140 to the fluid coupling network 170. In this embodiment, the fluid coupling network 170 further comprises a sixth controllable valve 210 fluidly coupled to the outlet of the third controllable valve 207 and to a port OP1 couplable to the processing system 160 and being configured to allow or prevent fluid to flow to the processing system 160. In this embodiment, the fluid coupling network 170 is controlled to provide the fluid sample and provide a fluid path by controlling the second controllable valve 206, the third controllable valve 207, the fifth controllable valve 205 and the sixth controllable valve 210 to an open operational state where fluid is allowed to flow, and controlling the first controllable valve 201 and the fourth controllable valve 209 to a closed operational state where fluid is prevented to flow.

Additionally or alternatively, the fluid coupling network 170 further comprises a seventh controllable valve 202 fluidly coupled to a third port IP3 couplable to a gas source 120 and being configured to allow or prevent gas to flow from the gas source 120 to the part of the fluid coupling network 170. In this embodiment, the fluid coupling network 170 is controlled to return residual fluid sample to the bioreactor 110 and provide a fluid path by controlling the first controllable valve 201 and the seventh controllable valve 202 to an open operational state where fluid is allowed to flow, and controlling the second controllable valve 206, the third controllable valve 207, the fourth controllable valve 209, the fifth controllable valve 205 and the sixth controllable valve 210 to a closed operational state where fluid is prevented to flow.

Additionally or alternatively, the fluid coupling network 170 further comprises an eighth controllable valve 211 fluidly coupled to an inlet of the second controllable valve 206 and the outlet of the third controllable valve 207 and being configured to allow or prevent fluid to flow between the inlet of the second controllable valve 206 and the outlet of the third controllable valve 207. In this embodiment, the fluid coupling network 170 is configured to fill 520 a section of the fluid coupling network and provide a fluid path by controlling the fifth controllable valve 205, the sixth controllable valve 210 and the eighth controllable valve 211 to an open operational state where fluid is allowed to flow, and controlling the first controllable valve 201, the second controllable valve 206, the third controllable valve 207, the fourth controllable valve 209 and the seventh controllable valve 202 to a closed operational state where fluid is prevented to flow.

Additionally or alternatively, the fluid coupling network 170 is configured to rinse the conduit reservoir 208 and provide a fluid path by controlling the second controllable valve 206, the third controllable valve 207, the fifth controllable valve 205 and the sixth controllable valve 210 to an open operational state where fluid is allowed to flow, and controlling the first controllable valve 201, the fourth controllable valve 209, the seventh controllable valve 202 and the eighth controllable valve 211 to a closed operational state where fluid is prevented to flow.

Additionally, or alternatively, the fluid coupling network 170 further comprises a ninth controllable valve 204 fluidly coupled to a fourth port IP4 couplable to a clean in place, CIP, source 130. In this embodiment, the fluid coupling network 170 is configured to clean the section of the fluid coupling network and provide a fluid path by controlling the sixth controllable valve 210, the eighth controllable valve 211 and the ninth controllable valve 204 to an open operational state where fluid is allowed to flow, and controlling the first controllable valve 201, the second controllable valve 206, the third controllable valve 207, the fourth controllable valve 209, the fifth controllable valve 205 and the seventh controllable valve 202 to a closed operational state where fluid is prevented to flow.

Additionally or alternatively, the fluid coupling network 170 is configured to clean the conduit reservoir 208 and provide a fluid path by controlling the second controllable valve 206, the third controllable valve 207, the fourth controllable valve 209 and the ninth controllable valve 204 to an open operational state where fluid is allowed to flow, and controlling the first controllable valve 201, the fifth controllable valve 205, the sixth controllable valve 210, the seventh controllable valve 202 and the eighth controllable valve 211 to a closed operational state where fluid is prevented to flow.

The fluid coupling network 170 may in one embodiment be provided with a housing and be arranged as an integrated unit.

The fluid coupling network 170 may in one embodiment be provided as an assembly of components, e.g. loose valves and conduits.

Figure 3:
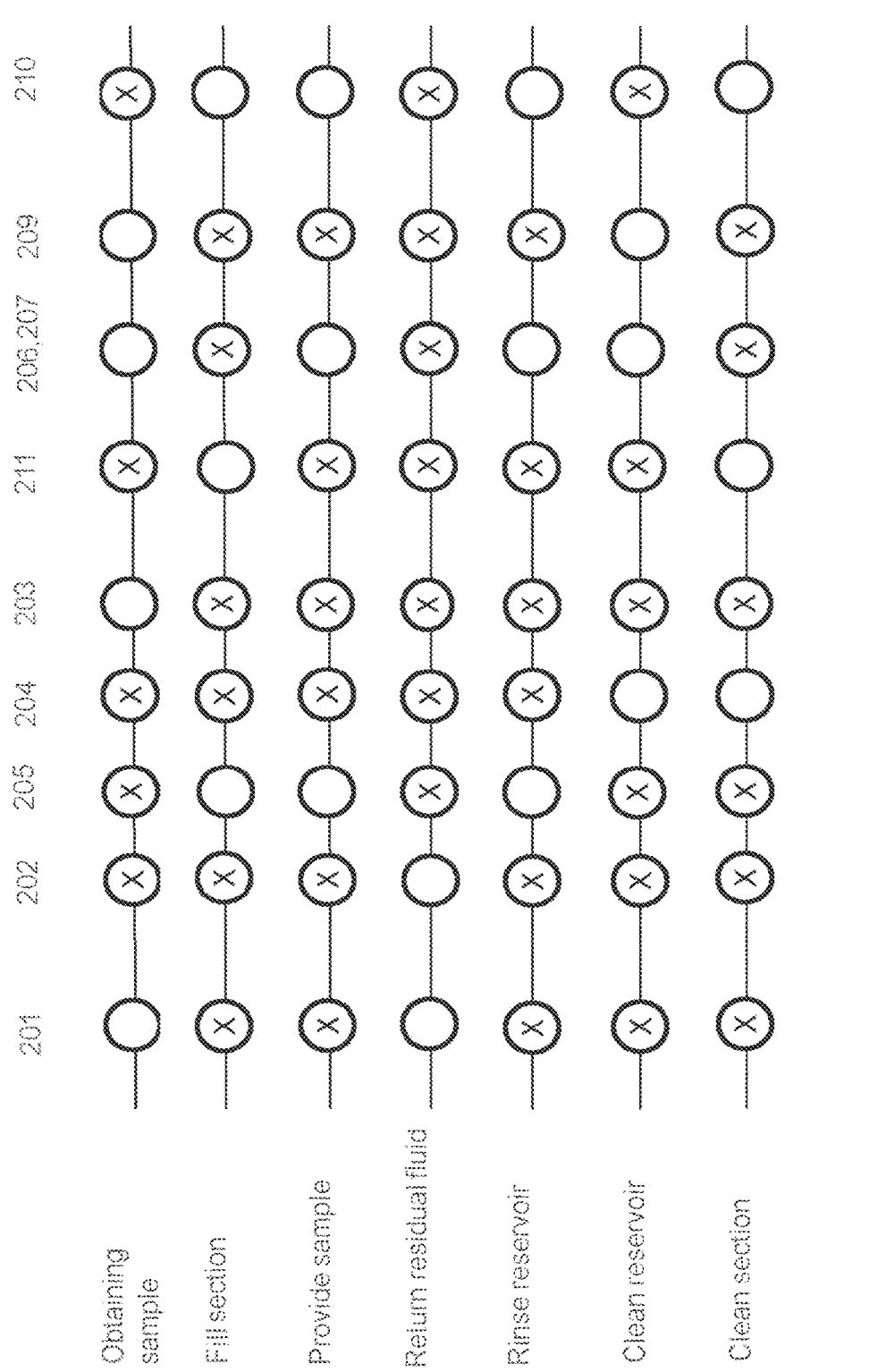
FIG. 3 illustrates operational states of controllable valves according to one or more embodiments of the present disclosure.

FIG. 3 illustrates operational states of controllable valves according to one or more embodiments of the present disclosure. Controllable valves in an open operational state is illustrated by an empty circle and controllable valves in a closed operational state is illustrated by a circle marked with an "X".

During the step of obtaining a sample, the first controllable valve 201, the second controllable valve 206, the third controllable valve 207 and the fourth controllable valve 209 are controlled to an open operational state. Remaining controllable valves are controlled to a closed operational state.

During the step of providing the sample, the second controllable valve 206, the third controllable valve 207, the fourth controllable valve 209 and the fifth controllable valve 205 are controlled to an open operational state.

During the step of returning residual fluid sample, the second controllable valve 206, the third controllable valve 207, the fourth controllable valve 209 and the fifth controllable valve 205 is controlled to an open operational state, the first controllable valve 201 and the seventh controllable valve 202 are controlled to an open operational state. Remaining controllable valves are controlled to a closed operational state.

During the step of filling the section of the fluid coupling network, the fifth controllable valve 205, the sixth controllable valve 210 and the eighth controllable valve 211 controlled to an open operational state. Remaining controllable valves are controlled to a closed operational state.

During the step of rinsing the reservoir 208, the second controllable valve 206, the third controllable valve 207, the fifth controllable valve 205 and the sixth controllable valve 210 are controlled to an open operational state. Remaining controllable valves are controlled to a closed operational state.

During the step of cleaning the reservoir, the second controllable valve 206, the third controllable valve 207, the fourth controllable valve 209 and the ninth controllable valve 204 are controlled to an open operational state. Remaining controllable valves are controlled to a closed operational state.

During the step of cleaning the section, the sixth controllable valve 210, the eighth controllable valve 211 and the ninth controllable valve 204 is controlled to an open operational state. Remaining controllable valves are controlled to a closed operational state.

Figure 4:
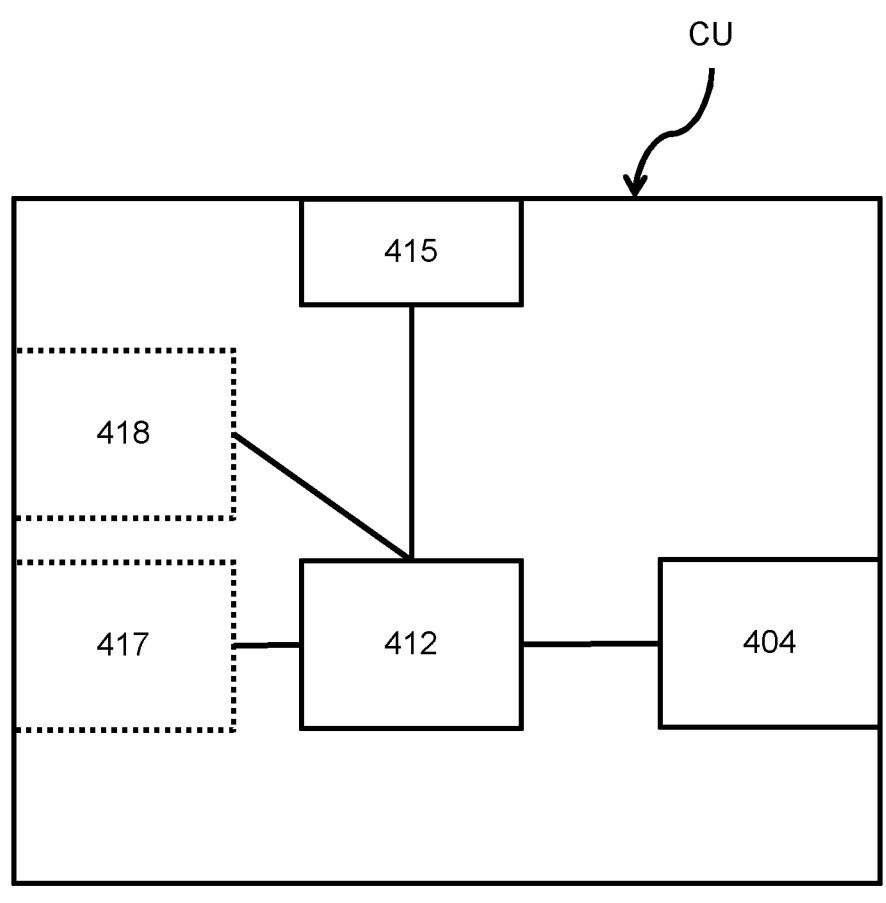
FIG. 4 shows a control unit according to one or more embodiments of the present disclosure.

FIG. 4 shows the control unit CU according to one or more embodiments of the present disclosure. The control unit CU may be in the form of a computer, e.g. an Electronic Control unit, a server, an on-board control unit, a stationary computing device, a laptop control unit, a tablet control unit, a handheld control unit, a wrist-worn control unit, a smart watch, a smartphone or a smart TV. The control unit CU may comprise processing circuitry 412 communicatively coupled to a communications interface, e.g. a transceiver 404, configured for wired or wireless communication. The control unit CU may further comprise at least one optional antenna (not shown in figure). The antenna may be coupled to the transceiver 404 and is configured to transmit and/or emit and/or receive wired or wireless signals in a communication network, such as Wi-Fi, Bluetooth, 3G, 4G, 5G etc. In one example, the processing circuitry 412 may be any of a selection of a processor and/or a central processing unit and/or processor modules and/or multiple processors configured to cooperate with each-other. Further, the control unit CU may further comprise a memory 415 communicatively coupled to the processing circuitry 412. The memory 415 may e.g. comprise a selection of a hard RAM, disk drive, a floppy disk drive, a flash drive or other removable or fixed media drive or any other suitable memory known in the art. The memory 415 may contain instructions executable by the processing circuitry to perform any of the steps or methods described herein. The processing circuitry 412 may be communicatively coupled to a selection of any of the transceiver 404 and the memory 415. The control unit CU may be configured to send/receive control signals directly to/from any of the above-mentioned units or to external nodes or to send/receive control signals via a wired and/or wireless communications network.

The wired/wireless transceiver 404 and/or a wired/wireless communications interface may be configured to send and/or receive data values or parameters as a signal to or from the processing circuitry 412 to or from other external nodes.

In an embodiment, the transceiver 404 communicates directly to external nodes or via the wireless communications network.

In one or more embodiments the control unit CU may further comprise an input device 417, configured to receive input or indications from a user and send a user input signal indicative of the user input or indications to the processing circuitry 412.

In one or more embodiments the control unit CU may further comprise a display 418 configured to receive a display signal indicative of rendered objects, such as text or graphical user input objects, from the processing circuitry 412 and to display the received signal as objects, such as text or graphical user input objects.

In one embodiment the display 418 is integrated with the user input device 417 and is configured to receive a display signal indicative of rendered objects, such as text or graphical user input objects, from the processing circuitry 412 and to display the received signal as objects, such as text or graphical user input objects, and/or configured to receive input or indications from a user and send a user-input signal indicative of the user input or indications to the processing circuitry 412.

In a further embodiment, the control unit CU may further comprise and/or be coupled to one or more additional sensors (not shown in the figure) configured to receive and/or obtain and/or measure physical properties pertaining to the bioprocessing system 100 and send one or more sensor signals indicative of the physical properties to the processing circuitry 412. An example of such an additional sensor may be an ambient air pressure sensor configured to measure the ambient air pressure where the bioprocessing system 100 is located.

In one or more embodiments, the processing circuitry 412 is further communicatively coupled to the input device 417 and/or the display 418 and/or the additional sensors.

In embodiments, the communications network communicate using wired or wireless communication techniques that may include at least one of a Local Area Network (LAN), Metropolitan Area Network (MAN), Global System for Mobile Network (GSM), Enhanced Data GSM Environment (EDGE), Universal Mobile Telecommunications System, Long term evolution, High Speed Downlink Packet Access (HSDPA), Wideband Code Division Multiple Access (W-CDMA), Code Division Multiple Access (CDMA), Time Division Multiple Access (TDMA), Bluetooth®, Zigbee®, Wi-Fi, Voice over Internet Protocol (VoIP), LTE Advanced, IEEE802.16m, WirelessMAN-Advanced, Evolved High-Speed Packet Access (HSPA+), 3GPP Long Term Evolution (LTE), Mobile WiMAX (IEEE 802.16e), Ultra Mobile Broadband (UMB) (formerly Evolution-Data Optimized (EV-DO) Rev. C), Fast Low-latency Access with Seamless Handoff Orthogonal Frequency Division Multiplexing (Flash-OFDM), High Capacity Spatial Division Multiple Access (iBurst®) and Mobile Broadband Wireless Access (MBWA) (IEEE 802.20) systems, High Performance Radio Metropolitan Area Network (HIPERMAN), Beam-Division Multiple Access (BDMA), World Interoperability for Microwave Access (Wi-MAX) and ultrasonic communication, etc., but is not limited thereto.

Moreover, it is realized by the skilled person that the control unit CU may comprise the necessary communication capabilities in the form of e.g., functions, means, units, elements, etc., for performing the present solution. Examples of other such means, units, elements and functions are: processors, memory, buffers, control logic, encoders, decoders, rate matchers, de-rate matchers, mapping units, multipliers, decision units, selecting units, switches, interleavers, de-interleavers, modulators, demodulators, inputs, outputs, antennas, amplifiers, receiver units, transmitter units, DSPs, MSDs, TCM encoder, TCM decoder, power supply units, power feeders, communication interfaces, communication protocols, etc. which are suitably arranged together for performing the present solution.

Especially, the processing circuitry of the present disclosure may comprise one or more instances of a processor, processor modules and multiple processors configured to cooperate with each-other, Central Processing Unit (CPU), a processing unit, a processing circuit, a processor, an Application Specific Integrated Circuit (ASIC), a microprocessor, a Field-Programmable Gate Array (FPGA) or other processing logic that may interpret and execute instructions. The expression "processing circuitry" and/or "processing means" may thus represent a processing circuitry comprising a plurality of processing circuits, such as, e.g., any, some or all of the ones mentioned above. The processing means may further perform data processing functions for inputting, outputting, and processing of data comprising data buffering and device control functions, such as call processing control, user interface control, or the like.

FIG. 5 shows a flowchart of a method 500 according to one or more embodiments of the present disclosure. The method may be performed by the fluid coupling network controlled by the control unit CU, the method comprising:

Step 510: obtaining a fluid sample from the bioreactor 110. In one embodiment, the step of obtaining the fluid sample comprises controlling a flow of fluid from the bioreactor 110 via the conduit reservoir 208 and the fluid coupling network 170 to the waste port 150, to fill the conduit reservoir 208 with the fluid from the bioreactor 110.

Step 530: providing the fluid sample, wherein the step of providing the fluid sample comprises to provide the fluid sample to the processing system 160 from the conduit reservoir 208 via the fluid coupling network 170.

Step 540: returning residual fluid sample to the bioreactor 110. In one embodiment, the residual fluid sample is comprised by a part of the fluid coupling network 170 separated by the barrier unit 220, wherein the step of returning residual fluid sample comprises controlling a flow of gas from a gas source 120 to the bioreactor 110 via the part of the fluid coupling network 170.

To prepare for the step of providing the fluid sample, a section of fluid paths comprised by the fluid coupling network 170 is filled with buffer fluid.

In one or more embodiments, the method further comprises filling 520 a section of the fluid coupling network by controlling a flow of buffer fluid from the buffer source 140 to the processing system 160 via the fluid coupling network 170.

After providing the fluid sample to the processing system 160, the conduit reservoir 208 is then rinsed to extract all of the fluid sample.

In one or more embodiments, the method further comprises rinsing 550 the conduit reservoir 208 by controlling a flow of buffer fluid from the buffer source 140 to the processing system 160 via the conduit reservoir 208 and the fluid coupling network 170.

To prepare the fluid coupling network 170 for the next sampling cycle, a section of the fluid coupling network 170 is cleaned.

In one or more embodiments, the fluid coupling network 170 further being configured to be fluidly couplable to a clean in place, CIP, source 130, the method further comprising cleaning the section of the fluid coupling network by controlling 560 a flow of cleaning fluid from the CIP source 130 to the processing system 160 via the fluid coupling network 170.

To prepare the fluid coupling network 170 for the next sampling cycle, the conduit reservoir 208 and related fluid paths of the fluid coupling network 170 is cleaned.

In one or more embodiments, the fluid coupling network 170 further being configured to be fluidly couplable to a clean in place, CIP, source 130, the method further comprising cleaning the conduit reservoir (208) by controlling (570) a flow of cleaning fluid from the CIP source (130) to the waste port (150) via the conduit reservoir (208) and the fluid coupling network (170).

As mentioned above, the barrier unit 220 is configured to sterilely separate fluid paths within the fluid coupling network 170. In particular, separating fluid paths of the fluid coupling network 170 into a part/first part 1701 and a remaining part/second part 1702. In other words, the barrier unit 220 is ensuring that no possibly contaminated fluid is returned to the bioreactor 110 and thereby interfere with the chemical process. Various embodiments of the barrier unit 220 are presented in FIG. 6-9.

Figure 6:
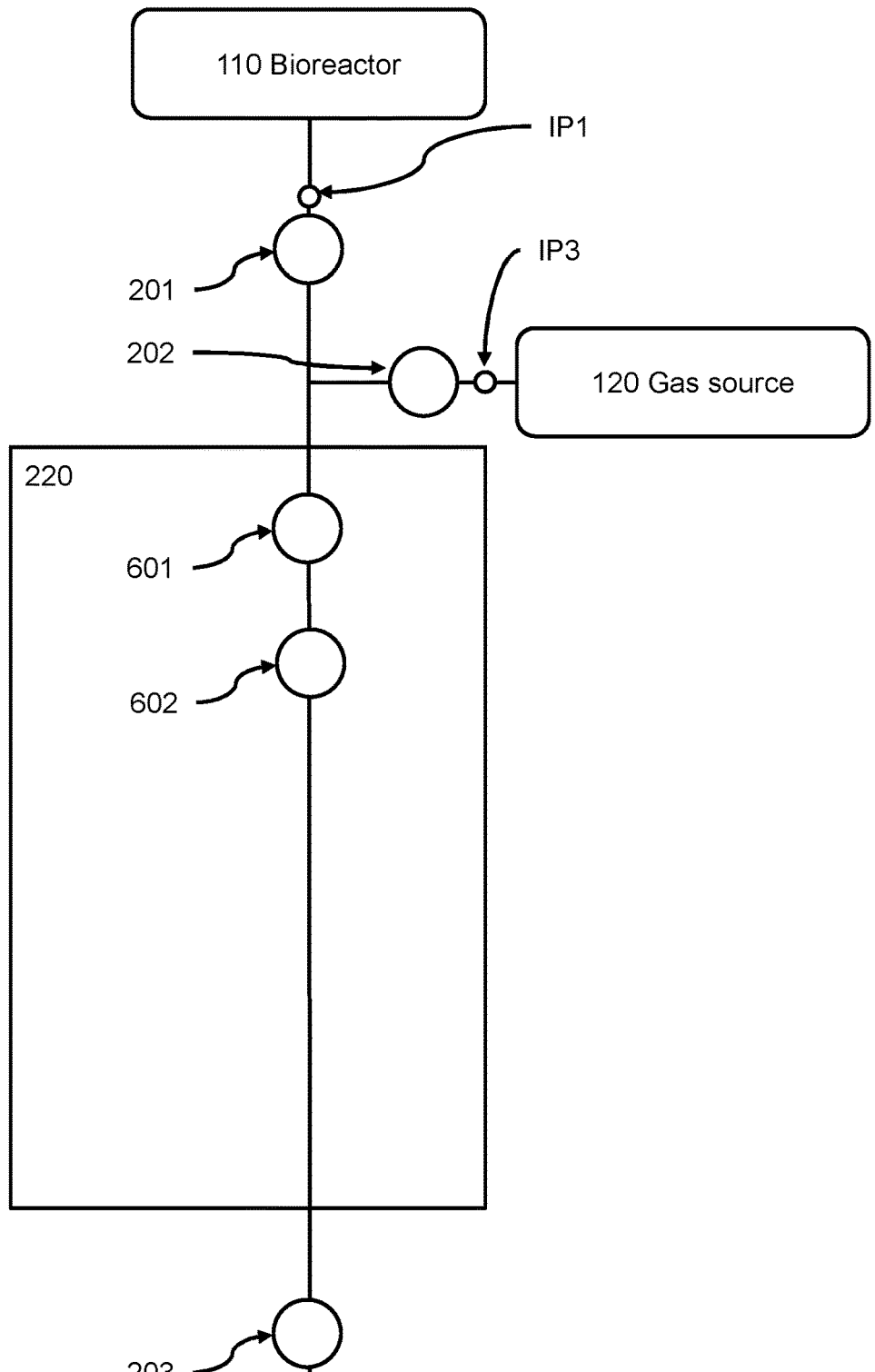
FIG. 6 shows an embodiment of the barrier unit according to one or more embodiments of the present disclosure.

FIG. 6 shows an embodiment of the barrier unit 220 according to one or more embodiments of the present disclosure. In one embodiment, the barrier unit 220 comprises at least two serially coupled valves 601, 602, operated in a sequential manner when transitioning between open and closed operational states. The transition of the valves between open and closed operational state is timed such that the last valve 602 is always closed before the valve before it 601, and always opened after the valve before it 601 is opened. This way, a "fluid-lock" of sorts is created and a one-directional flow from the bioreactor can be assured such that any contamination of the bioreactor originating from the remaining part 1702 can be avoided.

In one or more embodiments, a barrier unit 220 is provided that is configured to sterilely separate fluid paths within the fluid coupling network 170. The barrier unit 220 sterilely separates fluid paths of part/first part 1701 of the fluid coupling network 170 from fluid paths of a remaining part/second part 1702 of the fluid coupling network 170. The barrier unit 220, when operating in the first operational state, allows fluid to flow from the part/first part 1701 of the fluid coupling network 170 to the remaining part second part 1702 of the fluid coupling network 170. The barrier unit 220, when operating in the second operational state, prevents fluid to flow from the part/first part 1701 of the fluid coupling network 170 to the remaining part/second part 1702 of the fluid coupling network 170.

In one or more embodiments, the barrier unit 220 additionally comprises a tenth controllable valve 601 fluidly couplable to a fluid coupling network 170. The barrier unit 220 additionally comprises an eleventh controllable valve 602 fluidly couplable to a fluid coupling network 170. The tenth controllable valve 601 and the eleventh controllable valve 602 are configured to be controlled to an open operational state when the barrier unit 220 operates in the first operational state. The tenth controllable valve 601 is configured to be controlled to the open operational state before the eleventh controllable valve 602 is controlled to the open operational state. Alternatively, the tenth controllable valve 601 and the eleventh controllable valve 602 are configured to be controlled to a closed operational state when the barrier unit 220 operates in the second operational state. The tenth controllable valve 601 is configured to be controlled to the closed operational state after the eleventh controllable valve 602 is controlled to the closed operational state. A fluid path 604 is typically fluidly connecting an outlet of the eleventh controllable valve 602 to the remaining part/second part 1702 of the fluid coupling network 170.

In other words, the sequential control of the tenth controllable valve 601 and the eleventh controllable valve 602 ensures that any fluid pressure originating from the part/first part 1701 of the fluid coupling network 170 is applied to fluid in the fluid path between the tenth 601 and eleventh 602 controllable valves before any fluid pressure originating from the remaining part/second part 1702 of the fluid coupling network 170. Thereby the flow of fluid is kept unidirectional from the bioreactor to the remaining part/second part 1702 of the fluid coupling network 170.

In one embodiment, a flow sensor (not shown) is arranged in the fluid path between the tenth controllable valve 601 and the eleventh controllable valve 602. The flow sensor is configured to detect a reversed flow/a flow from the eleventh controllable valve 602 towards the tenth controllable valve 601 and send a control signal to the control unit CU. The control unit CU may then activate a visual or audio indication to a user of the system 100.

To further reduce the risk of contamination, some fluid paths 604 may be irradiated by a radiation source.

Figure 7:
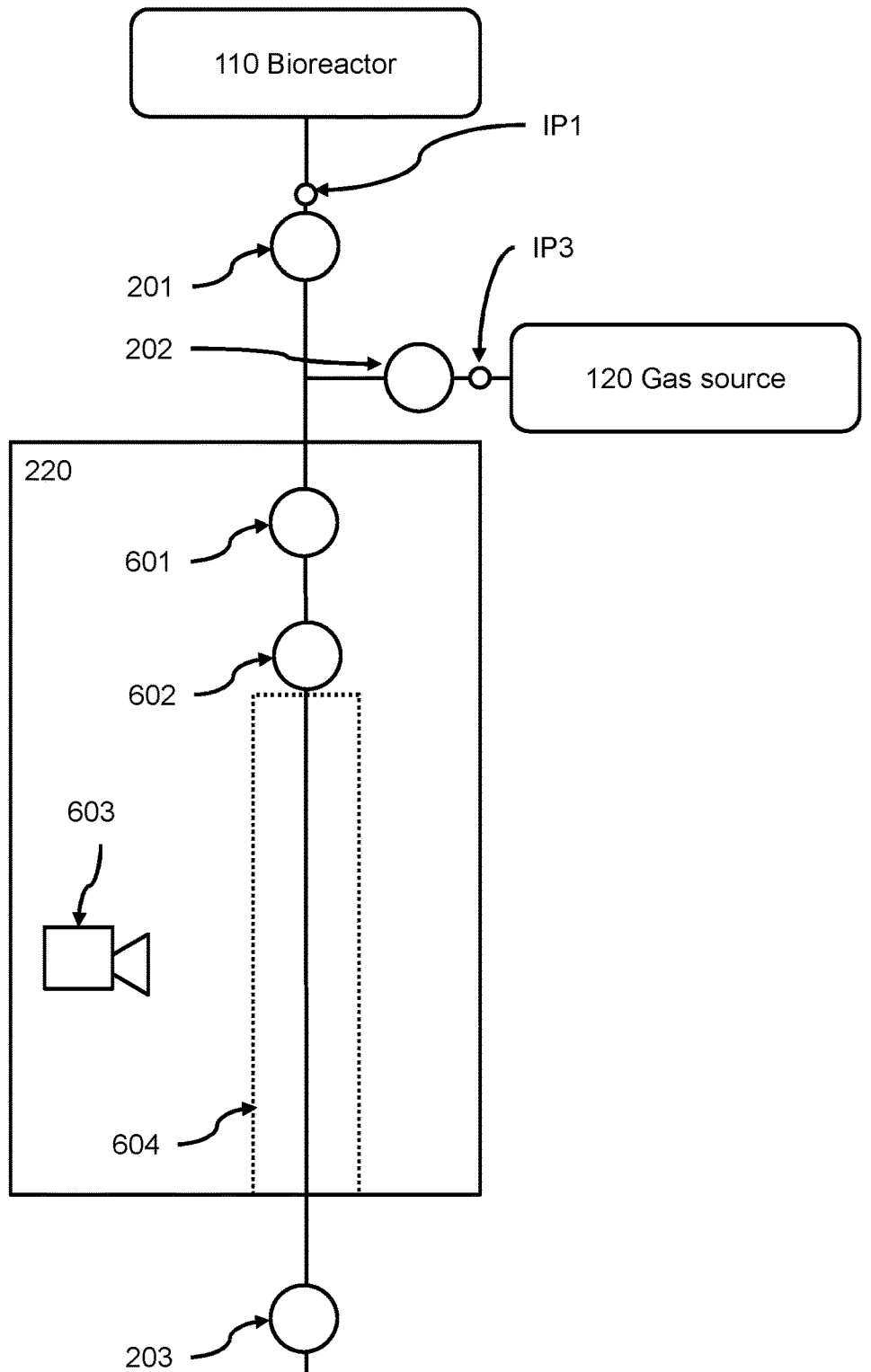
FIG. 7 shows yet an embodiment of the barrier unit according to one or more embodiments of the present disclosure.

FIG. 7 shows yet an embodiment of the barrier unit 220 according to one or more embodiments of the present disclosure.

In this embodiment, the barrier unit 220 further comprises a radiation source 603 configured to irradiate an inside of a fluid path 604 of the barrier unit 220 to sterilize the fluid path. Examples of radiation sources are ultraviolet, UV, light sources, such as an UV lamp or Light Emitting Diodes emitting UV light. The fluid path 604 is typically fluidly connecting an outlet of the eleventh controllable valve 602 to the remaining part/second part 1702 of the fluid coupling network 170.

To further reduce the risk of contamination, some fluid paths may further be subjected to negative pressure from a vacuum source 605. Examples of the vacuum source 605 is a vacuum pump, an ejector or a vacuum tank.

Figure 8:
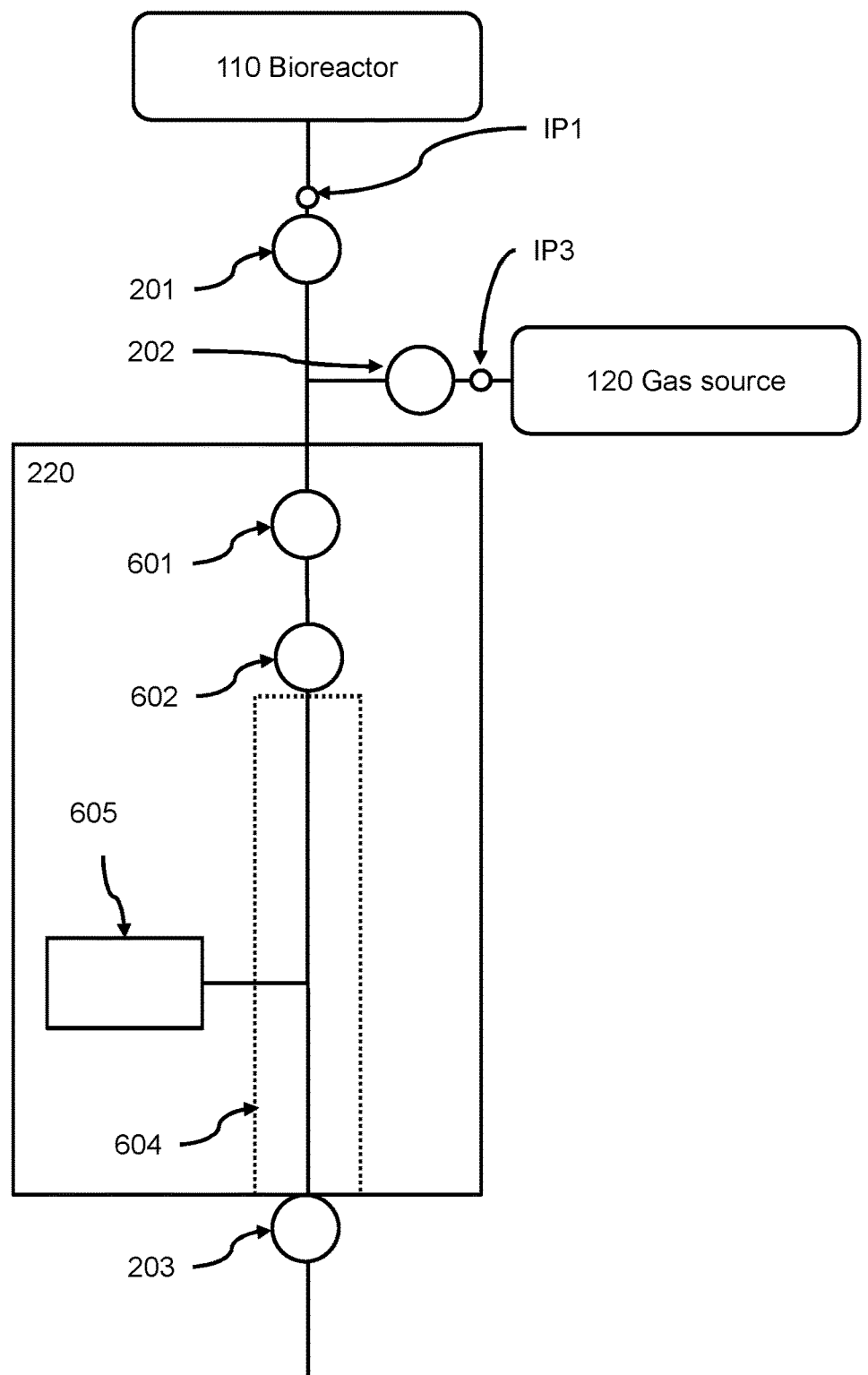
FIG. 8 shows yet an embodiment of the barrier unit according to one or more embodiments of the present disclosure.

FIG. 8 shows yet an embodiment of the barrier unit 220 according to one or more embodiments of the present disclosure.

In this embodiment, the barrier unit 220 further comprises a vacuum source 605 fluidly coupled to the fluid path 604 comprised by the barrier unit 220 and configured to receive fluid from the fluid path 604. The fluid path 604 is typically fluidly connecting an outlet of the eleventh controllable valve 602 to the remaining part/second part 1702 of the fluid coupling network 170.

To further reduce the risk of contamination, a constant flow of buffer fluid is maintained in some fluid paths.

Figure 9:
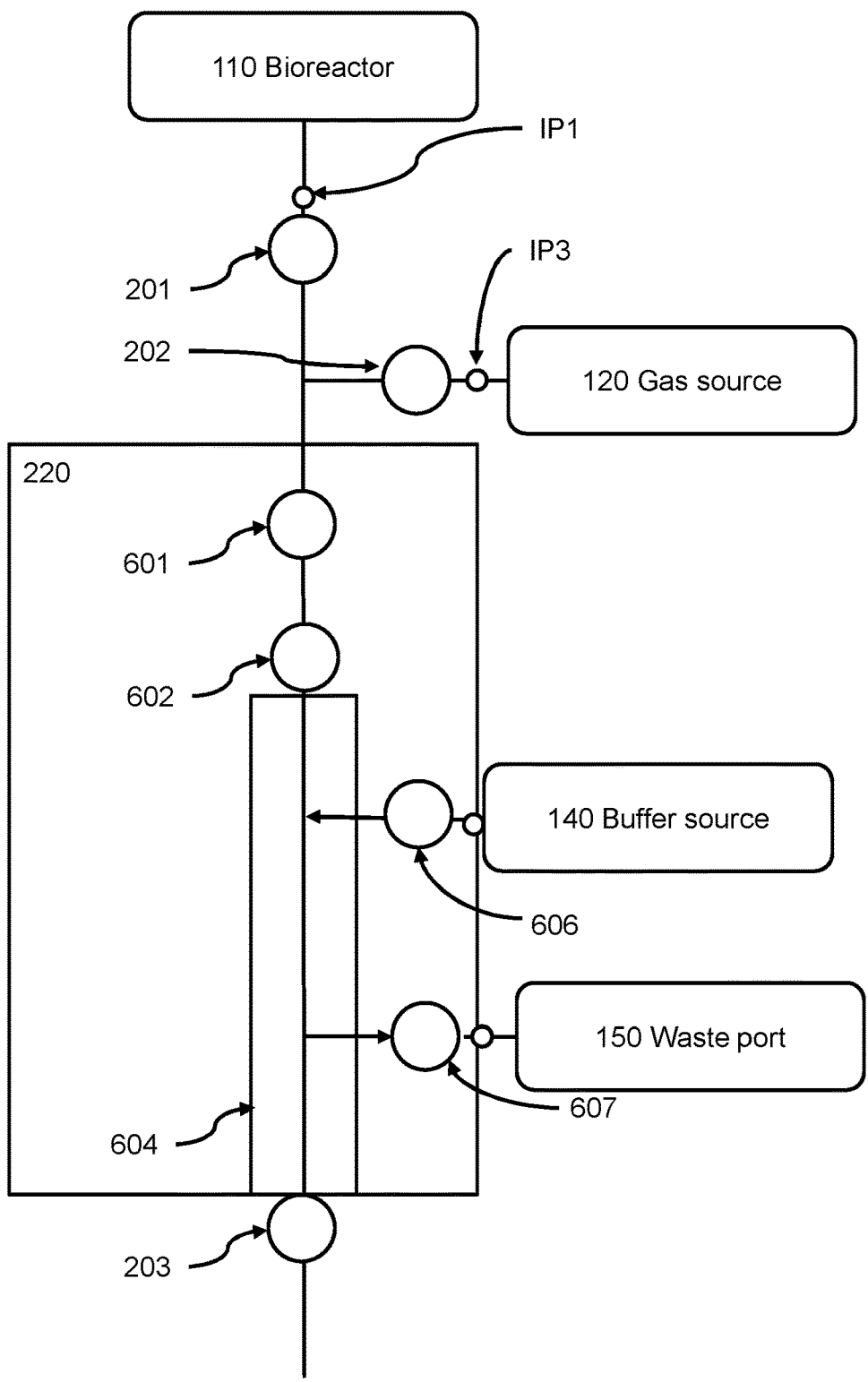
FIG. 9 shows yet an embodiment of the barrier unit according to one or more embodiments of the present disclosure.

FIG. 9 shows yet an embodiment of the barrier unit 220 according to one or more embodiments of the present disclosure.

In this embodiment, the barrier unit 220 according to any of the preceding claims, further comprises a twelfth controllable valve 606 fluidly couplable to a buffer source 140 and a thirteenth controllable valve 607 fluidly couplable to the waste port 150. The twelfth controllable valve 606 and the thirteenth controllable valve 607 are configured to be controlled to an open operational state when the barrier unit 220 operates in the first operational state. Alternatively, the twelfth controllable valve 606 and the thirteenth controllable valve 607 are configured to be controlled to a closed operational state when the barrier unit 220 operates in the second operational state.

It is understood that all the embodiments described in FIG. 6-9 may be combined in any combination without departing from the present disclosure In all the embodiments described in FIG. 6-9, the barrier unit 220 changes between the first operational state and the second operational state in response to a received control signal.

Finally, it should be understood that the invention is not limited to the embodiments described above, but also relates to and incorporates all embodiments within the scope of the appended independent claims.

The invention claimed is:

1. A computer implemented method for controlling a fluid coupling network, the fluid coupling network being configured to be fluidly couplable to bioreactor, a gas source, a buffer source, a waste port, a processing system and a conduit reservoir, the fluid coupling network comprising a barrier unit configured to sterilely separate fluid paths within the fluid coupling network, the fluid coupling network being controllable to sample the bioreactor, the method comprising:

obtaining a fluid sample from the bioreactor, wherein the step of obtaining the fluid sample comprises controlling a flow of fluid from the bioreactor via the conduit reservoir and the fluid coupling network to the waste port, to fill the conduit reservoir with the fluid from the bioreactor, providing the fluid sample, wherein the step of providing the fluid sample comprises to provide the fluid sample to the processing system from the conduit reservoir via the fluid coupling network, and returning residual fluid sample to the bioreactor, wherein the residual fluid sample is comprised by a part of the fluid coupling network separated by the barrier unit, wherein the step of returning residual fluid sample comprises controlling a flow of gas from a gas source to the bioreactor via the part of the fluid coupling network.

2. The method according to claim 1, the method further comprising filling a section of the fluid coupling network by controlling a flow of buffer fluid from the buffer source to the processing system via the fluid coupling network.

3. The method according to claim 1, the method further comprising rinsing the conduit reservoir by controlling a flow of buffer fluid from the buffer source to the processing system via the conduit reservoir and the fluid coupling network.

4. The method according to claim 1, the fluid coupling network further being configured to be fluidly couplable to a clean in place, CIP, source, the method further comprising cleaning the section of the fluid coupling network by controlling a flow of cleaning fluid from the CIP source to the processing system via the fluid coupling network.

5. The method according to claim 1, the fluid coupling network further being configured to be fluidly couplable to a clean in place, CIP, source, the method further comprising cleaning the conduit reservoir by controlling a flow of cleaning fluid from the CIP source to the waste port via the conduit reservoir and the fluid coupling network.

6. A barrier unit configured to sterilely separate fluid paths within a fluid coupling network, the fluid coupling network being configured to be fluidly couplable to a bioreactor and a gas source, wherein the barrier unit sterilely separates fluid paths of part of the fluid coupling network from fluid paths of a remaining part of the fluid coupling network, wherein the barrier unit, operating in a first operational state, allows fluid to flow from the part of the fluid coupling network to remaining part of the fluid coupling network and the barrier unit, operating in a second operational state, prevents fluid to flow from the part of the fluid coupling network to the remaining part of the fluid coupling network, and wherein the barrier unit is configured to sterilely separate the part of the fluid coupling network, the part comprising the fluid paths that fluidly couple the bioreactor and the gas source.

7. The barrier unit according to claim 6, further comprising:

a twelfth controllable valve fluidly couplable to a buffer source, a thirteenth controllable valve fluidly couplable to a waste port, wherein the twelfth controllable valve and the thirteenth controllable valve are configured to be controlled to an open operational state when the barrier unit operates in the first operational state, or wherein the twelfth controllable valve and the thirteenth controllable valve are configured to be controlled to a closed operational state when the barrier unit operates in the second operational state.

8. A control unit (CU) for a fluid coupling network being controllable to sample a bioreactor, the control unit comprising:

processing circuitry, a memory comprising instructions executable by the processing circuitry, causing the processing circuitry to perform the method according to claim 1.

9. A computer program comprising computer-executable instructions for causing a control unit, when the computer-executable instructions are executed on processing circuitry comprised in the control unit (CU), to perform any of the method steps according to claim 1.

10. A computer program product comprising a computer-readable storage medium, the computer-readable storage medium having the computer program according to claim 9 embodied therein.

11. A fluid coupling network, the fluid coupling network being configured to be fluidly couplable to bioreactor, a gas source, a buffer source, a waste port a processing system and a conduit reservoir, the fluid coupling network comprising a barrier unit configured to sterilely separate fluid paths within the fluid coupling network, the fluid coupling network being controllable to sample the bioreactor, wherein the fluid coupling network is configured to:

obtain a fluid sample, wherein the fluid sample is obtained by enabling a flow of fluid from the bioreactor by providing a fluid path from the bioreactor via the conduit reservoir to the waste port, to fill the conduit reservoir with fluid from the bioreactor, provide the fluid sample, wherein the fluid sample is provided to the processing system by providing a fluid path from the conduit reservoir to the processing system, and return residual fluid sample to the bioreactor, wherein the residual fluid sample is comprised by a part of the fluid coupling network separated by the barrier unit, wherein the residual fluid sample is returned by providing a fluid path from the gas source to the bioreactor, wherein the barrier unit is configured to sterilely separate the part of the fluid coupling network, the part comprising fluid paths that fluidly couple the bioreactor and the gas source.

12. The fluid coupling network according to claim 11, further comprising:

a first controllable valve fluidly coupled to a first port (IP1) couplable to the bioreactor and being configured to allow or prevent fluid to flow between the bioreactor and the fluid coupling network, a second controllable valve fluidly coupled to an outlet of the first controllable valve, and an inlet of the conduit reservoir, and being configured to allow or prevent fluid, received from any of the first controllable valve to flow to the conduit reservoir, a third controllable valve fluidly coupled to an outlet of the conduit reservoir, and being configured to allow or prevent fluid to flow from the conduit reservoir, a fourth controllable valve fluidly coupled to an outlet of the third controllable valve and to the waste port and being configured to allow or prevent fluid to flow from the outlet of the third controllable valve to the waste port, wherein the fluid coupling network is controlled to obtain a fluid sample and provide a fluid path by controlling the first controllable valve, the second controllable valve, the third controllable valve and the fourth controllable valve to an open operational state where fluid is allowed to flow.

13. The fluid coupling network according to claim 12, further comprising:

a fifth controllable valve fluidly coupled to a second port (IP2) couplable to the buffer source and being configured to allow or prevent fluid to flow from the buffer source to the fluid coupling network, and a sixth controllable valve fluidly coupled to the outlet of the third controllable valve and to a port (OP2) couplable to the processing system and being configured to allow or prevent fluid to flow to the processing system, wherein the fluid coupling network is controlled to provide the fluid sample and provide a fluid path by controlling the second controllable valve, the third controllable valve, the fifth controllable valve and the sixth controllable valve to an open operational state where fluid is allowed to flow, and controlling the first controllable valve and the fourth controllable valve to a closed operational state where fluid is prevented to flow.

14. The fluid coupling network according to claim 13, further comprising:

a seventh controllable valve fluidly coupled to a third port (IP3) couplable to a gas source and being configured to allow or prevent gas to flow from the gas source to the part of the fluid coupling network, and wherein the fluid coupling network is controlled to return residual fluid sample to the bioreactor and provide a fluid path by controlling the first controllable valve and the seventh controllable valve to an open operational state where fluid is allowed to flow, and controlling the second controllable valve, the third controllable valve, the fourth controllable valve, the fifth controllable valve and the sixth controllable valve to a closed operational state where fluid is prevented to flow.

15. The fluid coupling network according to claim 14, further comprising:

an eighth controllable valve fluidly coupled to an inlet of the second controllable valve and the outlet of the third controllable valve and being configured to allow or prevent fluid to flow between the inlet of the second controllable valve and the outlet of the third controllable valve, wherein the fluid coupling network is configured to fill a section of the fluid coupling network and provide a fluid path by controlling the fifth controllable valve, the sixth controllable valve and the eighth controllable valve to an open operational state where fluid is allowed to flow, and controlling the first controllable valve, the second controllable valve, the third controllable valve, the fourth controllable valve and the seventh controllable valve to a closed operational state where fluid is prevented to flow.

16. The fluid coupling network according to claim 15, wherein the fluid coupling network is configured to rinse the conduit reservoir and provide a fluid path by controlling the second controllable valve, the third controllable valve, the fifth controllable valve and the sixth controllable valve to an open operational state where fluid is allowed to flow, and controlling the first controllable valve, the fourth controllable valve, the seventh controllable valve and the eighth controllable valve to a closed operational state where fluid is prevented to flow.

17. The fluid coupling network according to claim 15, further comprising:

a ninth controllable valve fluidly coupled to a fourth port (IP4) couplable to a clean in place, CIP, source, wherein the fluid coupling network is configured to clean the section of the fluid coupling network and provide a fluid path by controlling the sixth controllable valve, the eighth controllable valve and the ninth controllable valve to an open operational state where fluid is allowed to flow, and controlling the first controllable valve, the second controllable valve, the third controllable valve, the fourth controllable valve, the fifth controllable valve and the seventh controllable valve to a closed operational state where fluid is prevented to flow.

18. The fluid coupling network according to claim 15, wherein:

the fluid coupling network is configured to clean the conduit reservoir and provide a fluid path by controlling the second controllable valve, the third controllable valve, the fourth controllable valve and the ninth controllable valve to an open operational state where fluid is allowed to flow, and controlling the first controllable valve, the fifth controllable valve, the sixth controllable valve, the seventh controllable valve and the eighth controllable valve to a closed operational state where fluid is prevented to flow.

19. The barrier unit according to claim 6, further comprising a vacuum source fluidly coupled to a fluid path comprised by the barrier unit and configured to receive fluid from the fluid path.

20. The barrier unit according to claim 6, comprising:

a tenth controllable valve fluidly couplable to a fluid coupling network, an eleventh controllable valve fluidly couplable to a fluid coupling network, wherein the tenth controllable valve and the eleventh controllable valve are configured to be controlled to an open operational state when the barrier unit operates in the first operational state, wherein the tenth controllable valve is configured to be controlled to the open operational state before the eleventh controllable valve is controlled to the open operational state, or wherein the tenth controllable valve and the eleventh controllable valve are configured to be controlled to a closed operational state when the barrier unit operates in the second operational state, wherein the tenth controllable valve is configured to be controlled to the closed operational state after the eleventh controllable valve is controlled to the closed operational state.

21. The barrier unit according to claim 20, further comprising: a radiation source configured to irradiate a fluid path of the barrier unit to sterilize the fluid path.

22. The barrier unit according to claim 6, wherein the barrier unit changes between the first operational state and the second operational state in response to a received control signal.

* * * * *